United States Patent [19]

Bacehowski et al.

[11] Patent Number: 4,968,624

[45] Date of Patent: Nov. 6, 1990

[54] LARGE VOLUME FLEXIBLE CONTAINERS

[75] Inventors: David Bacehowski, Wildwood; Arnold Bilstad, Deerfield; Michael R. Keilman, Mundelein, all of Ill.

[73] Assignee: Baxter International Inc., Deerfield, Ill.

[21] Appl. No.: 342,915

[22] Filed: Apr. 25, 1989

[51] Int. Cl.$^5$ .............................. C12M 1/00
[52] U.S. Cl. .................... 435/287; 435/284; 220/403; 206/484; 206/524.2
[58] Field of Search ................ 435/287, 296, 284; 604/408–410, 415; 206/5, 438, 484, 524.2; 383/37, 116; 428/35, 212; 220/465, 403

[56] References Cited

U.S. PATENT DOCUMENTS

| | | |
|---|---|---|
| 2,344,369 | 3/1944 | Salfisberg . |
| 2,898,027 | 8/1959 | Scholle . |
| 3,007,608 | 11/1961 | Cox, Jr. . |
| 3,112,047 | 11/1963 | Weinreich . |
| 3,137,415 | 6/1964 | Faunce . |
| 3,169,690 | 2/1965 | Scholle . |
| 3,204,825 | 9/1965 | Underwood . |
| 3,206,105 | 9/1965 | Smith . |
| 3,248,040 | 4/1966 | Friedman . |
| 3,269,278 | 8/1966 | Olstad . |
| 3,318,759 | 5/1967 | Anderson . |
| 3,521,806 | 6/1970 | Esty . |
| 3,734,394 | 5/1973 | Dooley . |
| 3,946,780 | 3/1976 | Sellers .................... 435/311 |
| 4,085,244 | 4/1978 | Stillman . |
| 4,119,267 | 10/1978 | Kydonieus . |
| 4,160,053 | 7/1979 | Clayton . |
| 4,212,299 | 7/1980 | Yokokoji et al. . |
| 4,324,333 | 4/1982 | Porter . |
| 4,381,776 | 5/1983 | Latham, Jr. . |
| 4,511,609 | 4/1985 | Craver et al. . |
| 4,557,959 | 12/1985 | Kuehlein et al. . |
| 4,558,801 | 12/1985 | Vilutis . |
| 4,561,110 | 12/1985 | Hebert .................... 604/408 |
| 4,643,926 | 2/1987 | Mueller . |
| 4,657,540 | 4/1987 | Iwamoto et al. .......... 604/408 |
| 4,686,125 | 8/1987 | Johnston et al. . |
| 4,700,838 | 10/1987 | Faociani et al. . |
| 4,775,562 | 10/1988 | Shishido et al. . |
| 4,786,192 | 11/1988 | Graves et al. . |
| 4,793,519 | 12/1988 | Voorhies, Jr. . |
| 4,804,363 | 2/1989 | Valeri . |
| 4,829,002 | 5/1989 | Pattillo et al. . |

Primary Examiner—Larry Jones
Attorney, Agent, or Firm—Bradford R. L. Price; Paul C. Flattery; Robert M. Barrett

[57] ABSTRACT

The present invention provides a large volume flexible container capable of containing a fluid to be maintained under sterile conditions. The container comprises an inner liner constructed from a polyolefin that defines an interior of the container and an outer liner constructed from a three-layer laminate. The laminate includes an inner layer constructed from a polyolefin that will, upon the application of sufficient energy, bond to the polyolefin of the inner liner, a middle layer constructed from a barrier material, and an outer layer; the inner liner and outer liner being sealed together along edges of the container. At least one tube member, for accessing the container, extends from a face of the container, and includes an end that is secured to the container, a length of flexible tubing for defining a channel through which fluid can flow, and a connector at a second end. A structure for housing the container is also provided.

19 Claims, 2 Drawing Sheets

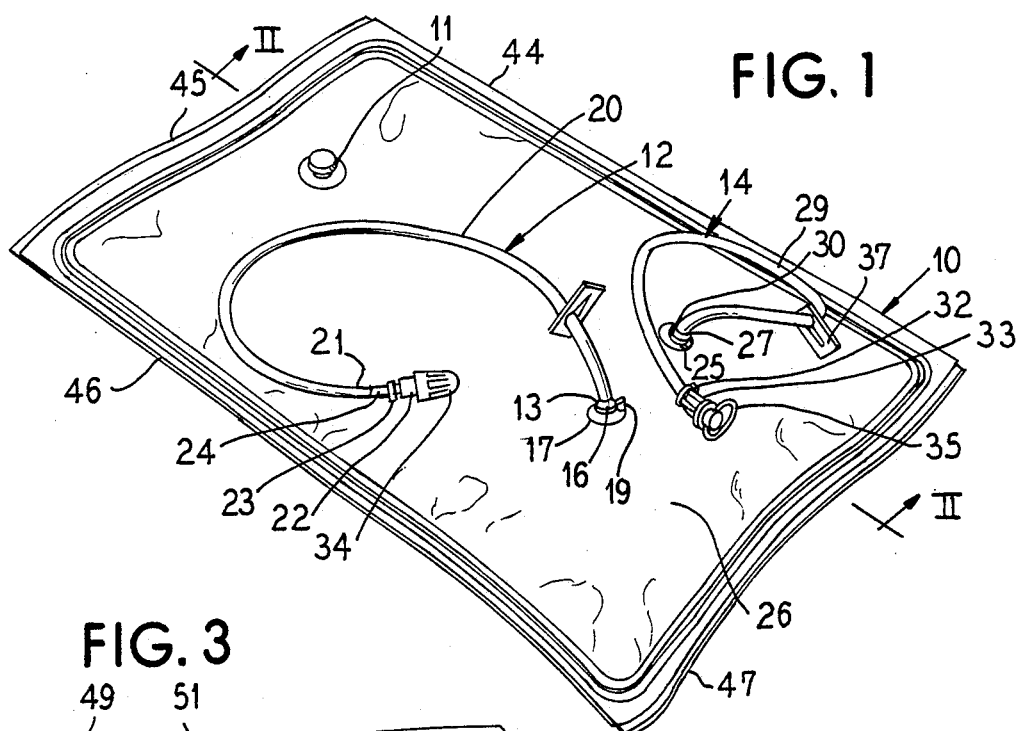
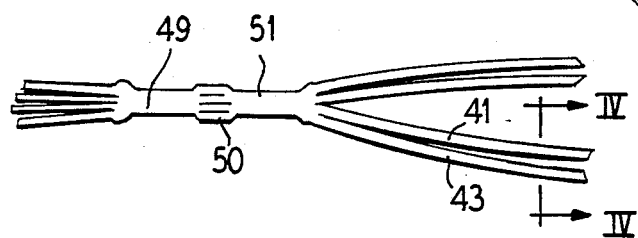
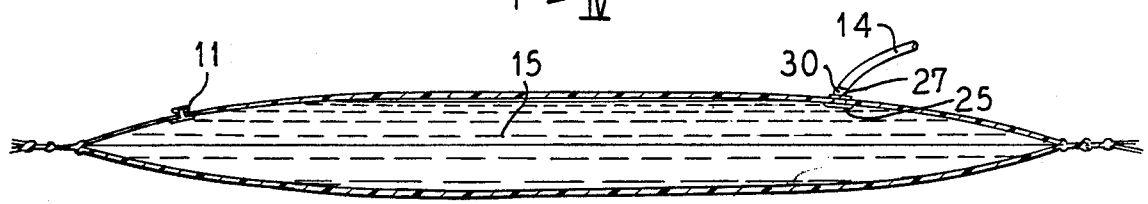
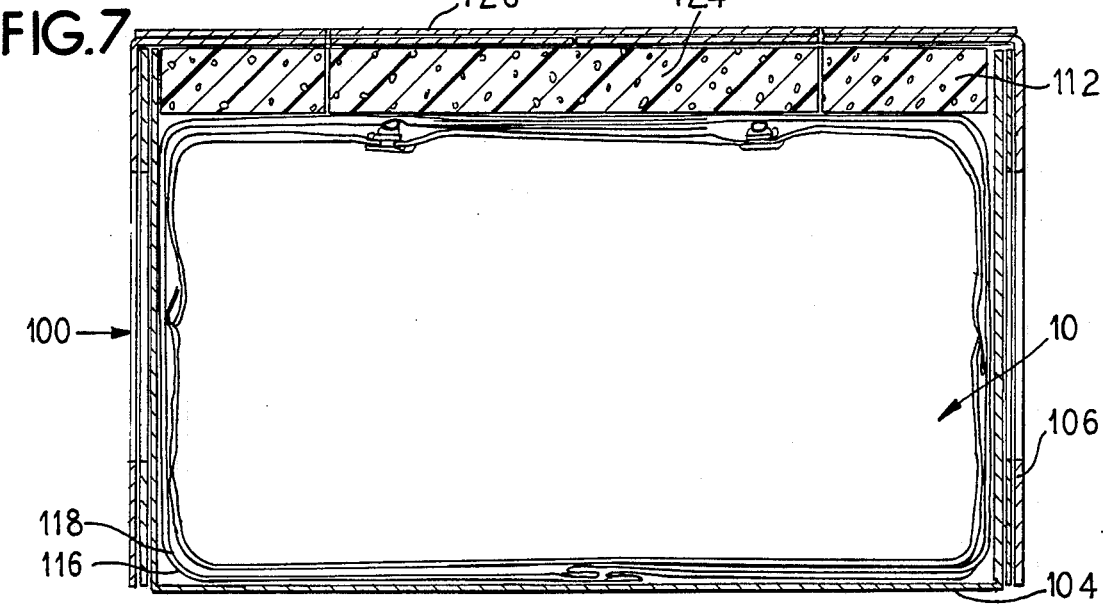

LARGE VOLUME FLEXIBLE CONTAINERS

BACKGROUND OF THE INVENTION

The present invention relates, in general, to flexible containers. More specifically, the present invention relates to containers for containing cell culture media, solutions, or the like.

In the culturing of cells, for example hybridoma cells, for manufacturing monoclonal antibodies or the like, it is necessary to provide cell culture media. Cell culture media is typically a solution of amino acids, electrolytes, and vitamins. It is known to supplement the solution with fetal bovine serum, which is believed to contain growth factors and other proteins that are essential to mammalian cell growth. The media is typically stored in either a liquid or powder form. If the media is in powder form, it must be reconstituted prior to use.

U.S. patent application Ser. No. 07/247,463, filed Sep. 21, 1988, now U.S. Pat. No. 4,910,147, issued 3/20/90 entitled: "CELL CULTURE MEDIA FLEXIBLE CONTAINER", discloses a flexible container for cell culture media. The media container comprises a body constructed from a flexible film that defines a containment area for containing the cell culture media. The body includes a front face and a back face. The front and back face are sealed to each other along at least three sides thereof. A fill port is provided for aseptically filling the containment area with cell culture media. The fill port is sealed to a face of the body and so constructed and arranged that it extends from the face, normal thereto.

Although the flexible container for cell culture media described in the above-identified patent application provides a container that can be utilized for many applications, a container having a different structure may be desirable in certain applications. For example, when a container is required for housing a large volume of fluid, e.g., five or more liters, the hydraulic forces exerted by the fluid within the container must be considered. In this regard, it should be noted that media containers are typically filled with media and then transported to the end user. During transportation, hydraulic forces can be generated by the fluid within the container that can act on the walls of the container. If a flexible container constructed from a web of film is utilized, these forces can cause the seals to fail and the material from which the container is constructed to delaminate.

One method utilized for shipping and/or transporting large volumes of cell culture media and solutions is to use rigid polycarbonate carboys. These rigid polycarbonate carboys, however, have the following disadvantages. They occupy significant storage space either when filled or empty. They require washing and sterilization by the customer. They utilize an open filling system and typically utilize a cumbersome, unreliable closure having a rubber stopper and tubing harness. Furthermore, venting is required for removal of the media and solution. Moreover, the carboys require special shipping cages/pallets. Still further, the containers experience significant breakage during shipping and handling.

It is also known to use recovery containers for cell culture solutions. The recovery containers are not filled by the manufacturer, but, rather, are supplied to the end user in an empty state to be filled, for example, utilizing a bioreactor.

Typical large volume recovery containers include expensive stainless steel tanks. These tanks must be washed, cleaned, sterilized, and de-pyrogenated, after each use. Similar to the polycarbonate carboys, these tanks also occupy significant storage space even when they are empty.

Accordingly, there is a need for an improved container for containing large volumes of cell culture media and the like.

SUMMARY OF THE INVENTION

The present invention provides a large volume flexible container capable of housing a fluid to be maintained under sterile conditions. The container affords a clear, flexible container for cell culture media and solution that can be provided to the end user or customer in a sterile and non-pyrogenic condition, having an integral tubing harness. The container allows an aseptic/sterile closed system processing without venting. In an empty state, the container is flat and has a space saving construction for easy storage. As a media container with an integral fill port it readily accommodates aseptic/sterile filling.

To this end, the container comprises an inner liner constructed from a polyolefin and an outer liner. The outer liner is constructed from a three-layer laminate having an inner layer constructed from a polyolefin that will, upon the application of sufficient energy, bond to the polyolefin of the inner liner, a middle layer constructed from a barrier material, and an outer layer. The inner liner and outer liner are sealed together along the edges of the container. At least one tube member for accessing the container is provided. The tube member extends from the container and includes an end that is secured to a face of the container, a length of flexible tubing for defining a channel through which liquid can flow, and a connector at a second end.

The container, due to its construction, provides long term stability to the cell culture media due to its gas and moisture barrier properties. Moreover, the inner liner is constructed from a biologically non-reactive and non-toxic material and therefore provides good fluid contact properties. Furthermore, the tube member, or harness, offers significant operating cost advantages.

In an embodiment of the invention, the inner liner is constructed from polyethylene and the three-layer laminate includes: an inner layer of polyethylene; a middle layer of ethylene-vinyl alcohol; and an outer layer of ethylene-vinyl acetate. In a preferred embodiment the polyethylene is linear low density polyethylene.

In an embodiment of the invention, the laminate includes two layers of a polyester adhesive for bonding the inner layer to the middle layer and the outer layer to the middle layer.

In an embodiment of the invention, the inner liner has a cross-sectional thickness of approximately 0.0005 to about 0.004 inches. In the embodiment, the outer liner has the following cross-sectional thicknesses: the inner layer has a cross-sectional thickness of approximately 0.0005 to about 0.004 inches; the middle layer has a cross-sectional thickness of approximately 0.0001 to about 0.002 inches; and the outer layer has a cross-sectional thickness of approximately 0.0005 to about 0.004 inches.

In an embodiment of the invention, at least two tube members, or assemblies, for accessing the interior of the container are provided. Preferably, one of the tube members includes a female luer connector and the other tube member includes a male luer connector.

In an embodiment of the present invention, a container capable of housing a fluid to be maintained under sterile conditions and box structure is provided. The container and box structure provides a unit that can withstand typical shipping demands and the hydraulic forces generated within the container. To this end, the box structure includes a top half and bottom half, the halves being so constructed and arranged that the bottom half is received with the top half to define a box. At least one liner is positioned within the bottom half of the box, the bottom half having a sufficient dimension to receive the container. The structure includes means for limiting movement of the container within the box during movement of the box.

In an embodiment of the invention, the means for limiting movement includes a resilient insert.

In an embodiment of the invention, an inner volume of the box approximates an outer volume of the container and its contents.

In an embodiment of the invention, means are provided for accessing the tube assembly without removing the container from the box.

In an embodiment of the invention, two liners are provided in the bottom half.

An advantage of the present invention is to provide an improved cell culture media or solution container.

A further advantage of the present invention is that it provides a cell culture media or solution container for containing at least five liters of fluid.

A still further advantage of the present invention is that it provides a container construction that will allow the flexible container to house a large volume of fluid without the container failing during transportation and storage of the container.

Still, an advantage of the present invention is that it provides a container and box construction that allows the container to contain a large volume of fluid and be transported without failing.

Moreover, an advantage of the present invention is that it provides a container and box construction conducive to use in a clean room or like environment.

Furthermore, an advantage of the present invention is that it provides a flexible container having a tubing harness integrally connected thereto that affords significant operating cost advantages as well as assists in maintaining sterility.

Further, an advantage of the present invention is that it provides a cell culture media container that affords for at least one year a long term stability of the cell culture media that is similar to that of a glass container.

Additional features and advantages of the present invention are described in, and will be apparent from, the detailed description of the presently preferred embodiments and from the drawings.

BRIEF DESCRIPTION OF THE DRAWINGS

FIG. 1 is a top elevational view of an embodiment of the large volume flexible container of the present invention.

FIG. 2 is a cross-sectional view taken along lines II—II of FIG. 1.

FIG. 3 is an enlarged view of a portion of the cross-sectional view of FIG. 2.

FIG. 7 is a cross-sectional view of the box structure of FIG. 6 taken along lines VII—VII of FIG. 6.

DETAILED DESCRIPTION OF THE PRESENTLY PREFERRED EMBODIMENTS

Figure 5:
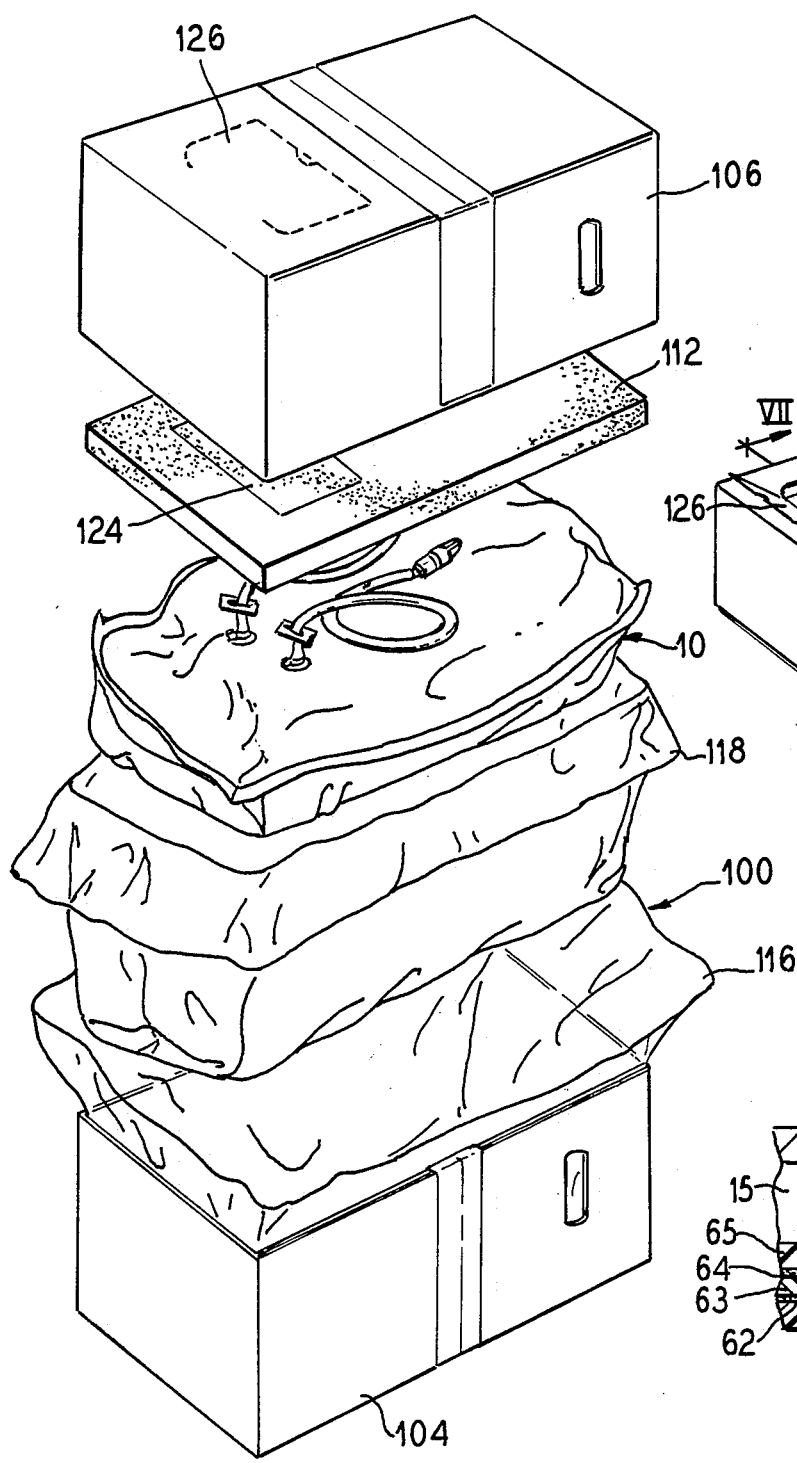
FIG. 5 is an exploded view of an embodiment of the present invention including a box structure for storing and/or transporting the large volume flexible container.

The present invention provides a large volume flexible container for cell culture media, solution, or the like. In this regard, the present invention provides, in an embodiment, a flexible container that can be used to store and/or transport cell culture media. In an embodiment, the present invention provides a recovery container.

Referring to FIG. 1, an embodiment of the container of the present invention is illustrated. The container 10, as set forth in detail infra, is constructed from flexible film and accordingly provides a flexible container. In the embodiment of the container illustrated, the container 10 includes a fill port 11, tube member 12, and tube member 14. The fill port 11 provides a means for filling the container 10 with cell culture media. Because for use of the container as a recovery container a fill port is not required, it should be noted that in an embodiment, the container 10 does not include a fill port. A fill port 11 available from M & D Industries, Inc., Brisbane, Calif., under the designation 16 mm Intasept fill port that includes a base membrane and allows the container to be filled and then is fully sealed has been found to function satisfactorily.

The tube members 12 and 14 are coupled or sealed to the container 10 and function to provide means for accessing an interior 15 of the container 10. In this regard, the tube member 12 includes, as illustrated in FIG. 1, an end portion 13 that is received over a barbed end 16 of a fitment 17 that is sealed to a front face 26 of the container 10. To this end, the end portion 13 is sufficiently resilient to be stretched over the barbed end 16 of the fitment 17. A clamp 19 is provided for securing the end 13 of the tube member 12 over the fitment 17.

The tube member 12 includes an elongated tube 20 having the first end 13 and a second end 21. In a preferred embodiment, the elongated tube 20 is constructed from a silicone material. The elongated tube 20 provides a fluid path from the first end 13 to the second end 21. Located at the second end 21 is a luer connector 22. In the embodiment illustrated, the connector 22 is a female luer connector designed to mate with a complementary male connector (not shown). Preferably, the connector 22 includes a portion 24 that is received within the second end 21 of the elongated tube 20 and secured therein by a clamp 23.

The second tube member 14 has a construction substantially similar to that of the first tube member 12. To this end, the second tube member 14 includes an elongated tube 29 that is secured at a first end 30 over a barbed end 27 of a fitment 25 that is secured to the front face 26 of the container 10. Likewise, the elongated tube 29 is preferably constructed of a silicone material that defines a fluid path for the flow of fluid either to or from the interior 15 of the container 10.

Located at a second end 32 of the tube connector 14 is a luer connector 33. The luer connector 33 is preferably a threaded male luer connector that is designed to mate with a complementary female connector (not shown).

Preferably, protective covers 34 and 35, respectively, cover the luer connectors 22 and 33. The protective covers 34 and 35 are designed to be removed by the user prior to use.

The tube members 12 and 14 define a tubing harness that provides a fluid flow path between the interior 15 of the container 10 and an exterior environment. Due to the elongated tube portions 20 and 29, dispensing to or from the container 10 can be performed either by the use of gravity or by pumping, for example, with a peristaltic pump. To prevent the flow of fluid from or to the container 10, members 37 can be utilized.

As previously stated, the container 10 is constructed from sheets of film. These sheets of film are sealed together to define the container 10.

Figure 4:
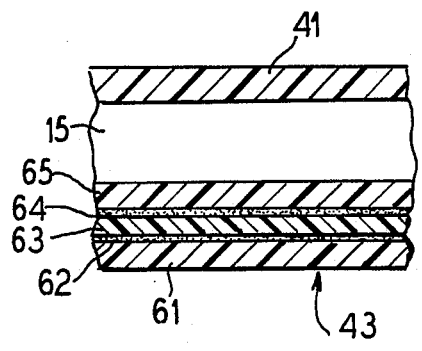
FIG. 4 is an enlarged cross-sectional view taken along lines IV—IV of FIG. 3.

Referring now to FIGS. 2, 3, and 4, the container 10 of the present invention includes a double walled construction. In this regard, an inner liner 41 and an outer liner 43 define the container 10. The inner and outer liners 41 and 43 are sealed to each other, as well as to corresponding film, to define the sides 44, 45, 46, and 47 of the container 10. In the embodiment of the invention illustrated, preferably, each edge or side 44, 45, 46, and 47 includes a double seal 49 and 51. To this end, seals 49 and 51 are defined along each of the edges with a non-sealed intermediate area 50 lying therebetween. This has been found to assist in allowing the container 10 to function as a large volume container as this seal structure can withstand the hydraulic forces generated by volumes of fluid in excess of five liters.

The inner liner 41 is preferably a single layer film. Preferably, the inner liner 41 is constructed from polyolefin. It should be noted that the inner liner 41 must, because it defines the interior 15 of the container 10 and is in direct fluid contact, be biocompatible and exhibit very low to no leachables/extractables. In a preferred embodiment, the inner liner 41 is constructed from a linear low density polyethylene.

Preferably, the inner liner has a cross-sectional thickness of between approximately 0.0005 to about 0.004 inches. In a most preferred embodiment, the inner liner has a cross-sectional thickness of approximately 0.002 inches. It has been found that these parameters of the inner liner 41 provide a film that will afford sufficient protection for housing the fluid contained therein and allow the liner to be sealed to the outer liner 43, and itself, forming the container 10.

With respect to the parameters and choices of film for the container 10 it should be borne in mind that the resultant container in addition to having sufficient strength and barrier properties must have sufficient clarity and be capable of being radiation sterilizable. With respect to clarity, pH indicators are typically utilized in the solutions to indicate a growth of contaminates and therefore, the container must have sufficient clarity to allow one to note any change in the pH indicator.

The outer liner 43 is preferably a laminate structure. To this end, the outer liner 43 includes three layers: an outer layer 61; a middle layer 63; and an inner layer 65. To seal the three layers 61, 63, and 65 together, two adhesive layers 62 and 64 are provided.

Preferably, the outer layer 61 is constructed from a polyolefin or polyester. The outer layer 61 must provide strength, flex crack resistance, and abuse protection for the container 10. In a preferred embodiment, the outer layer 61 is constructed from ethylene-vinyl acetate. The outer layer 61, in an embodiment, is constructed from polyester. In a most preferred embodiment, the outer layer is constructed from EVA having 5% vinyl acetate.

Preferably, the outer layer 61 has a cross-sectional thickness of approximately 0.0005 to about 0.004 inches. In a most preferred embodiment, the outer layer 61 has a cross-sectional thickness of approximately 0.002 inches. It has been found that these parameters provide sufficient strength to the film while still allowing the film to be sufficiently flexible and have clarity.

The middle layer 63 functions to provide barrier properties to the resultant container 10 to prevent oxygen ingress and carbon dioxide and moisture egress. The middle layer 63 is preferably constructed from material chosen from the group consisting of polyvinylidene chloride and ethylene-vinyl alcohol. In a preferred embodiment, the middle layer is constructed from biaxially oriented EVOH 47 gauge.

Preferably, the middle layer 63 has a cross-sectional thickness of approximately 0.0001 to about 0.002 inches. Most preferably, the middle layer 63 has a cross-sectional thickness of approximately 0.0005 inches. Again, these parameters have been found to provide a film that has sufficient clarity and flexibility as well as sufficient barrier properties.

The inner layer 65 of the outer liner 43 is preferably constructed from a polyolefin. This polyolefin should be compatible with the film structure of the inner liner 41 from the standpoint of allowing these two layers to be sealed together upon the application of sufficient energy. This will allow the inner and outer liners 41 and 43 to be sealed together along their edges to create the container 10. In a preferred embodiment, the inner layer 65 is constructed from linear low density polyethylene.

Preferably, the inner layer 65 has a cross-sectional thickness of approximately 0.0005 to about 0.004 inches. Most preferably, the inner layer 65 has a cross-sectional thickness of approximately 0.0002 inches. These parameters not only provide a film with clarity and flexibility, but also provide a film that can be securely sealed to the inner liner 41.

The outer, middle, and inner layers 61, 63, and 65, respectively, are sealed together by adhesive layers 62 and 64. The adhesive layers 62 and 64 must be radiation resistant so that the container 10 can be terminally sterilized prior to filling same. In this regard, the container 10 is preferably sterilized utilizing radiation. Preferably, the adhesive layers 62 and 64 are constructed from a polyester adhesive.

It has been found that the inner and outer liners 41 and 43 that comprise the container 10 provide a container having sufficient strength to house a large volume of fluid, for example, twenty liters, and allow same to be transported without the container 10 failing. Furthermore, the liners 41 and 43 create a container 10 having flexibility, sufficient clarity, and properties of biocompatibility and nonleachability that allow the container 10 to be utilized for housing cell culture media or solution.

Figure 6:
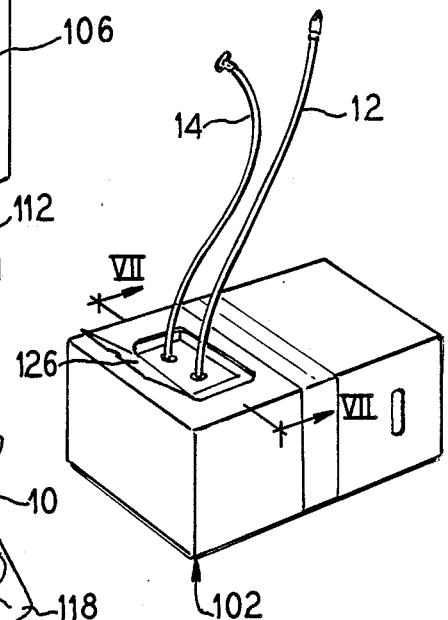
FIG. 6 is a top elevational view of the box structure of FIG. 5.

Referring now to FIGS. 5-7, the container 10 of the present invention and means for housing the container and transporting same are illustrated. Due to the large volume of fluid to be housed typical means for packaging the container and transporting same cannot be utilized without an unacceptably high failure rate of the container 10 occurring. In this regard, hydraulic forces generated by movement of the fluid during transportation of the container 10 can cause flex cracking and other failures of the container to occur. Furthermore, due to the environments within which the container 10 may be utilized, certain storage means may not be desirable for storing the container 10.

Referring now specifically to FIG. 5, an exploded view of structure 100 for transporting and storing the container 10 is illustrated. The structure 100 includes a box 102 having a bottom half 104 and a top half 106. The bottom half 104 is designed to be securely received within the top half 106 of the box 102. The box 102 preferably has a corrugated construction. A material available from International Paper, Northlake, Ill. under the designation ANVILBOX has been found to function satisfactorily for constructing the box.

Located within the bottom half 104 of the box 102, in the embodiment illustrated, is a first plastic liner 116. Located within the first plastic liner 116 is a second plastic liner 118. This double liner construction provides a construction that is conducive for use in clean rooms and other such environments.

In this regard, in clean roms and other environments, corrugated materials, due to the particulate and fibers generated thereby, cannot be brought into these environments. As illustrated in FIGS. 5 and 7, the double liner structure 116 and 118 allows the user to open the box 102 by removing the top half of the box 106, open the first liner 116, and then remove the second liner 118 and carry same into the clean room or other environment. Accordingly, the cleanliness of the container 10 is maintained and corrugated material or particulate generated therefrom is not brought into the clean room.

Preferably, the liners 116 and 118 are constructed from polyethylene, most preferably linear low density polyethylene.

It has been found that one of the principal concerns in transporting a large volume flexible container is movement of the container. Hydraulic forces generated in the container due to movement of the fluid within the container can result in movement of the container and can cause flex cracking of the container. These flex cracks can result in a failure of the container. Accordingly, the inner volume of the structure 100 should mirror, to the extent possible, the outer volume of the container 10 when the container contains the cell culture media.

However, due to certain tolerances, inherent therein, an exact duplication of this outer volume of the container 10 is not possible. Accordingly, the structure 100 includes a resilient insert 112. The resilient insert, as illustrated in FIG. 7, is positioned on top of the liners 116 and 118 after these liners are folded over the container 10. The bottom half 104 of the box 102 is then inserted in the top half 106 of the box 102. This results in the container 10 being securely positioned within the structure 100 preventing the movement of the container 10 in response to hydraulic forces.

The structure 100 is so constructed and arranged that it allows the end user to access the container 10 while it is still housed within the structure 100. To this end, the resilient insert 112 includes a removable portion 124 that corresponds to a flap portion 126 in the top half 106 of the box 102. Accordingly, by lifting the flap 126 one can access the removable portion 124 of the insert 112, and by peeling back the inner liners 116 and 118 can access the tube members 12 and 14. Therefore, in those environments where particulate and corrugated fibers in particular are not a concern, the container 10 can be accessed and utilized while in the structure 100. Due to the ability to telescope the box 102, the structure allows admixing while the container remains in the box 102.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A large volume flexible container capable of containing a fluid to be maintained under sterile conditions comprising:
   an inner liner constructed from a polyolefin that defines an interior of the container;
   an outer liner constructed from a three-layer laminate, having an inner layer constructed from a polyolefin that will, upon the application of sufficient energy, bond to the polyolefin of the inner layer, a middle layer constructed from a barrier material, and an outer layer, the inner liner and outer liner being sealed together along edges of the container; and
   at least one elongated tube member, for accessing the container, extending from a face of the container, and including an end that is secured to the container, a length of flexible tubing for defining a channel through which fluid can flow, and a connector at a second end for coupling the tube member to a second connector to provide fluid communication between the channel and a channel coupled to the second connector.

2. The container of claim 1 wherein the laminate includes two layers of a polyester adhesive for bonding the inner layer to the middle layer and the outer layer to the middle layer.

3. The container of claim 1 wherein:
   the inner liner has a cross-sectional thickness of approximately 0.0005 to about 0.004 inches; and
   in the outer liner, the inner layer has a cross-sectional thickness of approximately 0.0005 to about 0.004 inches, the middle layer has a cross-sectional thickness of approximately 0.0001 to about 0.002 inches, and the outer layer has a cross-sectional thickness of approximately 0.0005 to about 0.004 inches.

4. The container of claim 1 including a fill port for filling the interior of the container.

5. A large volume flexible container capable of containing a fluid to be maintained under sterile conditions comprising:
   an inner liner constructed from polyethylene that defines an interior of the container;
   an outer layer constructed from a three-layer laminate, the three-layer laminate includes an inner layer of polyethylene, a middle layer of ethylene-vinyl alcohol, and an outer layer of ethylene-vinyl acetate, the inner liner and outer liner being sealed together along edges of the container; and
   at least one tube member, for accessing the container, extending from a face of the container, and including an end that is secured to the container, a length of flexible tubing for defining a channel through which fluid can flow, and a connector at a second end.

6. The container of claim 5 wherein the polyethylene is linear low density polyethylene.

7. The container of claim 5 wherein the ethylene-vinyl acetate is biaxially oriented.

8. A large volume flexible container for containing a fluid to be maintained under sterile conditions having a fluid capacity of at least five liters, comprising:

an inner liner constructed from polyethylene, for defining an inner chamber for storing a fluid;

an outer liner sealed to the inner liner to define a container having an inner and outer liner, the outer liner being constructed from a three-layer laminate having an inner layer constructed from a polyethylene, a middle layer constructed from a material chosen from the group consisting of ethylene-vinyl alcohol and polyvinylidene chloride, and an outer layer constructed from a material chosen from the group consisting of ethylene-vinyl acetate and polyester; and at least two tube assemblies for accessing an interior of the container, the tubing assemblies having a first end coupled to a face of the container, a second end including a connector, and an elongated tube located between the first and second end for defining a channel for the flow of fluid therethrough, one tubing assembly including a male luer connector and a second tubing assembly including a female luer connector.

9. The container of claim 8 wherein:

the inner liner has a cross-sectional thickness of approximately 0.0005 to about 0.004 inches; and in the outer liner, the inner layer has a cross-sectional thickness of approximately 0.0005 to about 0.004 inches, the middle layer has a cross-sectional thickness of approximately 0.0001 to about 0.002 inches; and the outer layer has a cross-sectional thickness of approximately 0.0005 to about 0.004 inches.

10. The container of claim 8 wherein the polyethylene of the inner liner and the inner layer is linear low density polyethylene.

11. The container of claim 8 wherein the male luer connector and female luer connector include removable protective covers.

12. The container of claim 8 wherein the elongated tube is constructed from a silicone material.

13. The container of claim 8 wherein the container has secured to the face of the container two fitments and the first end of each of the tube assembly is coupled to a fitment.

14. The container of claim 13 wherein each fitment includes a barbed end.

15. The container of claim 8 wherein the container includes a fill port.

16. A container and a box structure capable of housing a fluid to be maintained under sterile conditions comprising:

a container comprising an inner liner constructed from a polyolefin that defines an interior of the container, and an outer liner constructed from a three-layer laminate, having an inner layer constructed from a polyolefin that will, upon the application of sufficient energy, bond to the polyolefin of the inner liner, a middle layer constructed from a barrier material, an outer layer, the inner liner and outer liner being sealed together to define edges of the container, and the container including at least one tube assembly extending from a face of the container for accessing an interior of the container; and a box structure including a top half and bottom half, the top half and bottom half being so constructed and arranged that the bottom half is received within the top half to define a box, at least one liner positioned within the bottom half of the box, the bottom half having a sufficient dimension to receive the container, the top half and bottom half cooperating to enclose the entire container and including means for accessing the tube assembly without removing the container from the box the container, and means for limiting movement of the container within the box during movement of the box.

17. The container and box structure of claim 16 wherein the means for limiting movement includes a resilient insert.

18. The container and box structure of claim 16 wherein an inner volume of the box approximates an outer volume of the container and its contents.

19. The container and box structure of claim 16 including two liners in the bottom half.

* * * * *